United States Patent
Hofmann

(10) Patent No.: US 8,926,599 B2
(45) Date of Patent: Jan. 6, 2015

(54) MEDICAL INSTRUMENT

(71) Applicant: Richard Wolf GmbH, Knittlingen (DE)

(72) Inventor: Adrian Hofmann, Pforzheim (DE)

(73) Assignee: Richard Wolf GmbH, Knittlingen (DE)

( * ) Notice: Subject to any disclaimer, the term of this patent is extended or adjusted under 35 U.S.C. 154(b) by 9 days.

(21) Appl. No.: 13/705,796

(22) Filed: Dec. 5, 2012

(65) Prior Publication Data

US 2013/0150665 A1 Jun. 13, 2013

(30) Foreign Application Priority Data

Dec. 8, 2011 (DE) .......................... 10 2011 088 003

(51) Int. Cl.
| | | |
|---|---|---|
| A61B 1/018 | (2006.01) | |
| A61B 17/29 | (2006.01) | |
| A61B 17/00 | (2006.01) | |
| A61B 19/00 | (2006.01) | |

(52) U.S. Cl.
CPC ............ *A61B 1/018* (2013.01); *A61B 17/2909* (2013.01); *A61B 2017/0046* (2013.01); *A61B 2017/292* (2013.01); *A61B 2017/2923* (2013.01); *A61B 2019/4868* (2013.01)
USPC .......................................................... 606/1

(58) Field of Classification Search
CPC ............... A61B 19/22; A61B 19/2203; A61B 2019/2242; A61B 17/29; A61B 17/00234; A61B 17/2909; A61B 1/018; A61B 2017/0046; A61B 2017/292; A61B 2017/2923
See application file for complete search history.

(56) References Cited

U.S. PATENT DOCUMENTS

| | | | |
|---|---|---|---|
| 5,176,699 A | | 1/1993 | Markham |
| 5,282,806 A | * | 2/1994 | Haber et al. .................. 606/139 |
| 5,690,673 A | * | 11/1997 | Koscher et al. ............... 606/205 |
| 5,700,270 A | * | 12/1997 | Peyser et al. .................. 606/142 |
| 5,928,255 A | * | 7/1999 | Meade et al. ................. 606/170 |
| 6,425,906 B1 | | 7/2002 | Young et al. |
| 2006/0287641 A1 | * | 12/2006 | Perlin .............................. 606/1 |
| 2007/0179524 A1 | * | 8/2007 | Weber et al. .................. 606/205 |
| 2007/0287993 A1 | * | 12/2007 | Hinman et al. .................... 606/1 |
| 2008/0046003 A1 | * | 2/2008 | Renger et al. ................. 606/206 |
| 2010/0063437 A1 | * | 3/2010 | Nelson et al. .................. 604/35 |
| 2010/0312227 A1 | * | 12/2010 | House ............................ 604/544 |
| 2011/0152887 A1 | * | 6/2011 | Surti et al. .................... 606/142 |

FOREIGN PATENT DOCUMENTS

| | | |
|---|---|---|
| DE | 2845213 B2 | 11/1980 |
| DE | 19508186 C2 | 1/1998 |
| DE | 202007000427 U1 | 3/2007 |
| GB | 2073022 A | 10/1981 |

OTHER PUBLICATIONS

Office Action issued Sep. 12, 2012 in DE Application No. 10 2011 088 003.8.
Extended European Search Report issued Apr. 3, 2013 in EP Application No. 12193321.2.

* cited by examiner

*Primary Examiner* — Gary Jackson
*Assistant Examiner* — Boniface N Nganga
(74) *Attorney, Agent, or Firm* — Panitch Schwarze Belisario & Nadel LLP

(57) ABSTRACT

A medical instrument in the form of an endoscopic shank instrument includes an actuation element which is axially displaceable in a shank. Two lever arms are pivotably articulated in a manner distanced to one another and are positioned at a proximal side of the shank. The lever arms form part of a grip part. The lever arms are coupled in movement to the actuation element and are coupled directly to one another.

9 Claims, 7 Drawing Sheets

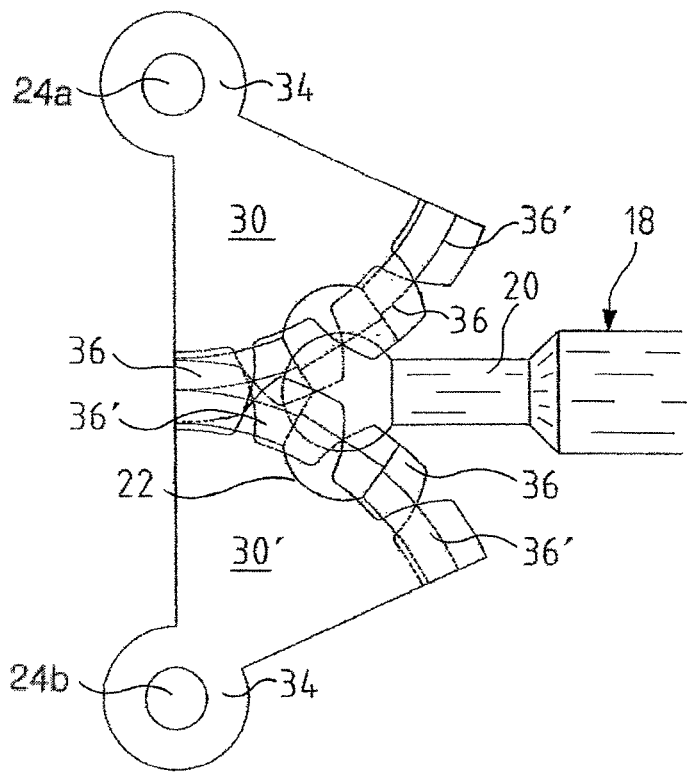
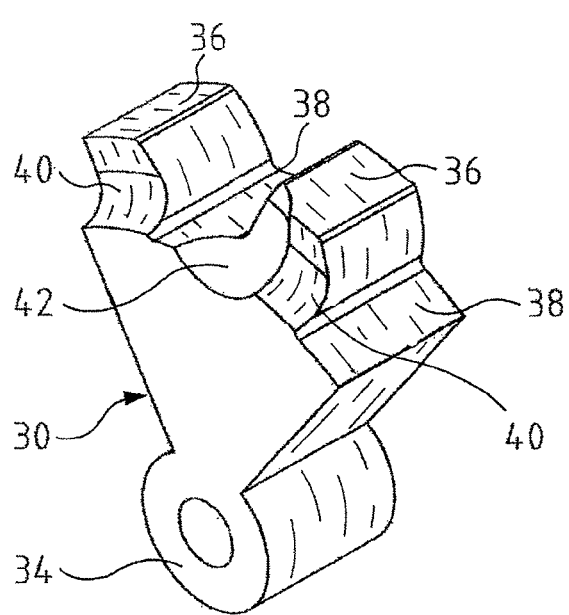

MEDICAL INSTRUMENT

BACKGROUND OF THE INVENTION

The present invention relates to a medical instrument.

Medical instruments are known from DE 665 208 and FR 688 681. For example, conventional medical instruments include an axially movable actuation element coupled in movement to two pivotable grip parts arranged distanced to one another, and this coupling movement is such that the actuation element, by way of the movement of the grip parts to one another, is displaced in a first direction and by way of the movement away from one another is displaced into a second direction which is opposite to this.

The movement coupling of the actuation element to the grip parts with these instruments is effected by way of a proximal end section of the actuation element being designed as a rack with teeth on two longitudinal sides which are away from one another, wherein a region which is designed on both grip parts in a cog-like manner is engaged on each of these teeth. The pivoting movements of the two grip parts are synchronized by way of the simultaneous engagement of the cog-like regions of the grip part into the teeth formed on the sides of the actuation element.

With the known instruments, it has been found to be disadvantageous that their manufacture requires quite some effort. A further disadvantage of these instruments is the fact that for a removal of the actuation element from the instrument, for example for maintenance purposes, it is necessary to disassemble the grip parts prior to this.

BRIEF SUMMARY OF THE INVENTION

Against the above background, it is an objective of a preferred embodiment of the present invention to provide a medical instrument of the type mentioned above, which has a simpler construction compared to the instruments known until now, and whose actuation element can be disassembled and assembled in a simpler manner.

The above objective is achieved by a medical instrument with an actuation element which is axially displaceable in a shank and with two lever arms which are pivotably articulated in a manner distanced to one another, at the proximal side of the shank and which in each case form part of a grip part, wherein the lever arms are coupled in movement to the actuation element and directly to one another. Advantageous developments of this instrument are to be deduced from the subsequent description as well as the drawings. Hereby, according to a preferred embodiment of the present invention, the features specified in the dependent claims, in each case per se, but also in combination, can further contribute to the inventive solution according to the independent claim(s).

With the medical instrument according to a preferred embodiment of the present invention, it is preferably the case of an endoscope shank instrument, for example of an endoscopic gripper forceps, coagulation forceps or scissors. The instrument includes an actuation element which is axial displaceable in a shank. This preferably rod-like actuation element can on the distal side be coupled in movement to a tool arranged at the distal end of the instrument and particularly advantageously to a forceps branch or scissor branch arranged there in a pivotably movable manner, which together with a forceps branch or scissor branch arranged stationarily or rigidly on the distal end of the instrument, forms a forceps jaw or scissor jaw.

The instrument according to a preferred embodiment of the present invention on the proximal side of the shank comprises two lever arms which are pivotably articulated in a manner distanced to one another. Each of these lever arms is part of a grip part for actuating the instrument. According to a preferred embodiment of the present invention, the lever arms are coupled in movement to the actuation element and directly to one another. This means that in contrast to that which was common until now, the grip parts are not coupled in movement to one another indirectly via the actuation element, but directly to one another, so that the movement coupling of the two lever arms of these grip parts to one another which is necessary for the synchronization of the pivot movements of the grip parts, is effected independently of the movement coupling of the lever arms to the actuation element. This permits the movement coupling of the lever arms to the actuation element to be formed in a manner which is simpler with regard to design, and moreover permits a construction of the actuation element which is simpler with regard to manufacturing technology, on which actuation element on the proximal side for example merely a simple catch can be formed, said catch being able to be actively connected to the lever arms in such a manner that a pivoting movement of the lever arms directly coupled in movement to one another causes a linear movement of the actuation element. Further advantageously, the movement coupling of the lever arms to the actuation element and which is separate from the movement coupling of the two lever arms to one another, by way of a suitable pivot movement of the lever arms which lies outside the pivot region of the lever arms necessary of actuating the instrument, permits the possibility of releasing the movement coupling of the lever arms to the actuation element, while the direct movement coupling of the lever arms to one another remains. In this manner, the actuation element can be disassembled and subsequently assembled gain in a simple manner if necessary.

Preferably, rolling surfaces rolling on one another are formed on sides of the lever arms which face one another, for creating the direct movement coupling of the two lever arms to one another. With this design, the rolling surfaces on the lever arms and which contact one another are arranged on an outer side facing the pivot axis of the respective other lever arm. Advantageously, the rolling surfaces are designed arc-shaped, wherein a middle axis of the rolling surfaces corresponds to the pivot axis of the respective lever arm. Further preferably, the two circular rolling surfaces have an equally large radius, so that no step-down transmission or step-up transmission of the movement coupling of the two lever arms takes place.

Basically, it is possible for the rolling surfaces of the two lever arms which roll on one another to form a friction pairing, so that the movement coupling of the two lever arms to one another is effected with a friction fit. However, a design with which the movement coupling of the two lever arms is effected with a positive fit is more preferable. In this context, one advantageously envisages the rolling surfaces of the two lever arms being designed in a toothed manner, wherein the teeth formed on the two rolling surfaces are engaged with one another.

According to a further advantageous development of the instrument according to a preferred embodiment of the present invention, the actuation element is preferably guided between the rolling surfaces. The guiding of the actuation element is hereby of the type such that the rolling surfaces always contact at least one a part region and thus create a direct movement coupling of the two lever arms to one another.

In each case, a groove is advantageously formed on the outside on the two rolling surfaces, for guiding the actuation element between the rolling surfaces. The grooves in each case as an arc extend over the rolling surfaces and are preferably arranged in the pivot plane of the two lever arms or on a plane which is parallel thereto. Together, the grooves form a receiver space for the actuation element or a guide channel which is closed in the direction transverse to the longitudinal extension of the actuation element.

Preferably, the actuation element is also coupled in movement to the two levers arm via a positive-fit connection. For this purpose, advantageously a widening, preferably a spherical widening can be formed on the actuation element and this widening engages into two recesses formed on the rolling surfaces. With regard to the widening formed on the actuation element, it is preferably the case of a region which is arranged at the proximal end of the actuation element and which has a widened cross section with respect to a section of the actuation element which connects thereto on the distal side. The recesses provided on the rolling surfaces of the two lever arms are each arranged in the region of the grooves formed on the rolling surfaces, wherein a middle axis of the recess running in the longitudinal direction of the rolling surface corresponds in each case to a middle axis of the groove. If the two rolling surfaces roll on one another by way of a simultaneous pivoting of the pivot arms, the position of the recesses formed on the rolling surfaces changes, by which means the widening engaging into the two recesses and thus, entailed by this, the complete actuation element is moved linearly in a certain region.

Preferably, the rolling surfaces are designed divided into two in the direction of the pivot axes of the lever arms, wherein teeth formed on the first part is designed offset by a tooth gap or tooth thickness with respect to teeth formed on a second part. Hereby, the division of the rolling surfaces into two is usefully effected in the direction of the pivot axis of the lever arms. Tooth gaps are located on the second part of the rolling surfaces, on the peripheral sections of the rolling surfaces, on which teeth are formed on the first part of the rolling surfaces, and teeth are located on the second part of the rolling surfaces, on the peripheral sections of the rolling surfaces, on which tooth gaps are formed on the first part of the rolling surfaces. Hereby, the teeth formed on the first part of the rolling surfaces, and the teeth formed on the second part of the rolling surfaces usefully have an equal tooth profile and tooth gap profile The teeth which are offset to one another in the two parts of the rolling surfaces have the advantage that teeth with a comparatively large module can be used for forming the two teeth of the rolling surface, so that the tooth gaps of the individual teeth are relatively large and thus can form a large part of the recesses for receiving the widening formed on the actuation element. Simultaneously, the offset arrangement of the teeth permits a partly play-free movement-coupling of the two lever arms to one another.

A design, with which the rolling surfaces in a second part of the rolling surfaces includes teeth offset to the first part of the rolling surfaces can be manufactured in a particularly simple manner, if as is further preferably envisaged, in each case two cog segments form the rolling surface of a lever arm, wherein all cog segments are designed equal with regard to construction. For example, the instrument according to a preferred embodiment of the present invention as a whole includes four constructionally equal cog segments.

Usefully, the cog segments have asymmetric teeth. This means the teeth formed on a cog segment begins with a tooth and ends with a tooth gap. For creating rolling surfaces divided in two and which in a first part have teeth arranged offset with respect to the second part, two cog segments are to be arranged above one another, wherein a second cog segment is aligned rotated by 180° about an axis running in the radius direction of the cog segment, with respect to a first cog segment.

It has been found that cog segments which are provided with two teeth and two tooth gaps are sufficient for realizing the axial displacement paths of the actuation element which is necessary with the medical instrument according to a preferred embodiment of the present invention, wherein the teeth formed on the cog segment extends over an angular range of 65°. Inasmuch as this is concerned, one envisages a design of the cog segments, with which the cog segments advantageously include two teeth and two tooth gaps in each case, wherein they further advantageously enclose an angle of 65°.

The cog segments are preferably integrated into grip parts for actuating the instrument according to a preferred embodiment of the present invention. Thus a recess, in which two cog segments are arranged over one another in the manner described above, can be formed on each of the two grip parts. Moreover, the two cog segments of a grip part can also be peripherally injected with a plastic forming the grip part.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 5 is a basic representation of the engagement conditions of the two cog segments and the actuation element in the operating part according to FIG. 1, in a third engagement position;

FIG. 9 is a perspective individual representation of a cog segment.

DETAILED DESCRIPTION OF THE INVENTION

Figure 1:
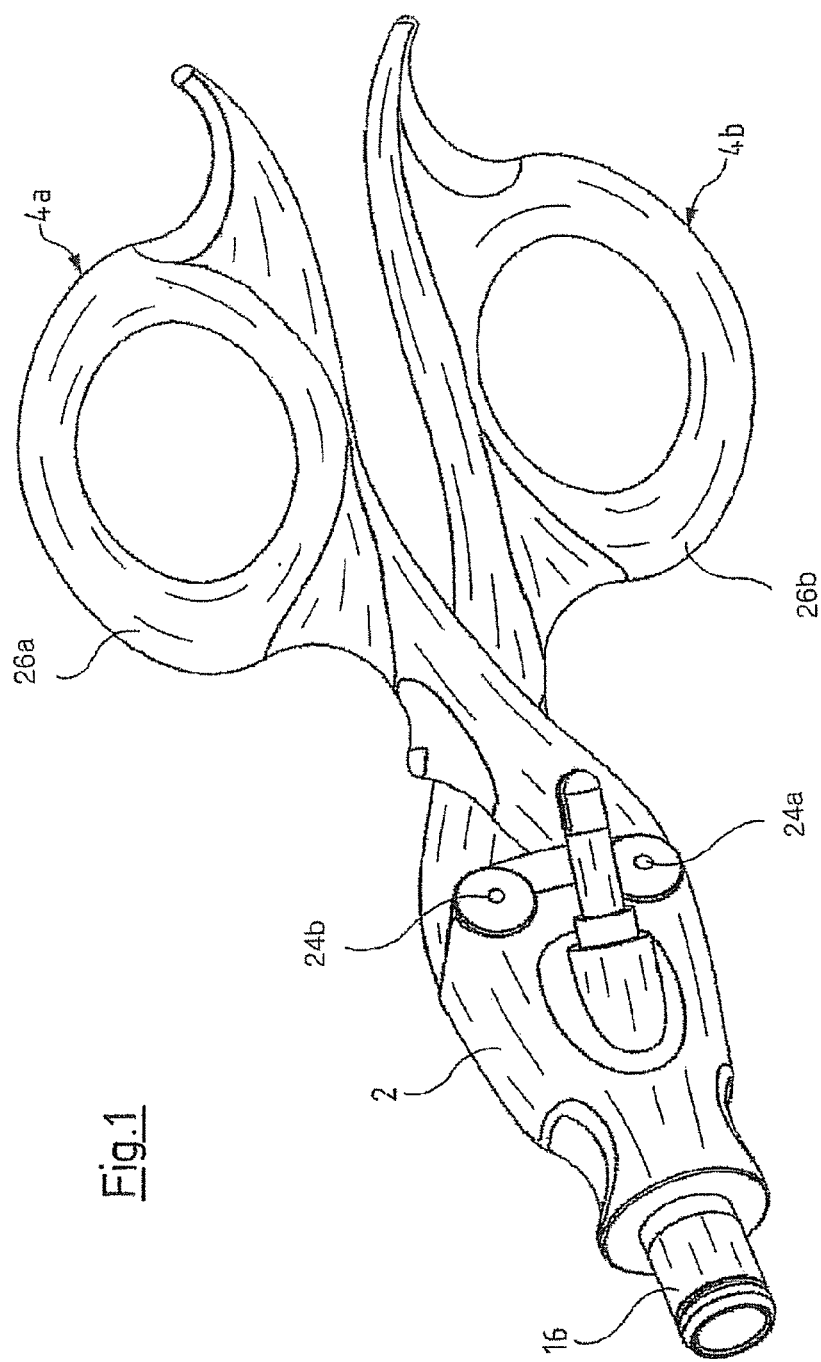
FIG. 1 is a schematically simplified perspective view of an operating part of a medical instrument according to a preferred embodiment of the present invention.

Certain terminology is used in the following description for convenience only and is not limiting. The words "right" and "left" designate directions in the drawings to which reference is made. Unless specifically set forth herein, the terms "a," "an" and "the" are not limited to one element, but instead should be read as meaning "at least one." The terminology includes the words noted above, derivatives thereof and words of similar import.

Figure 2:
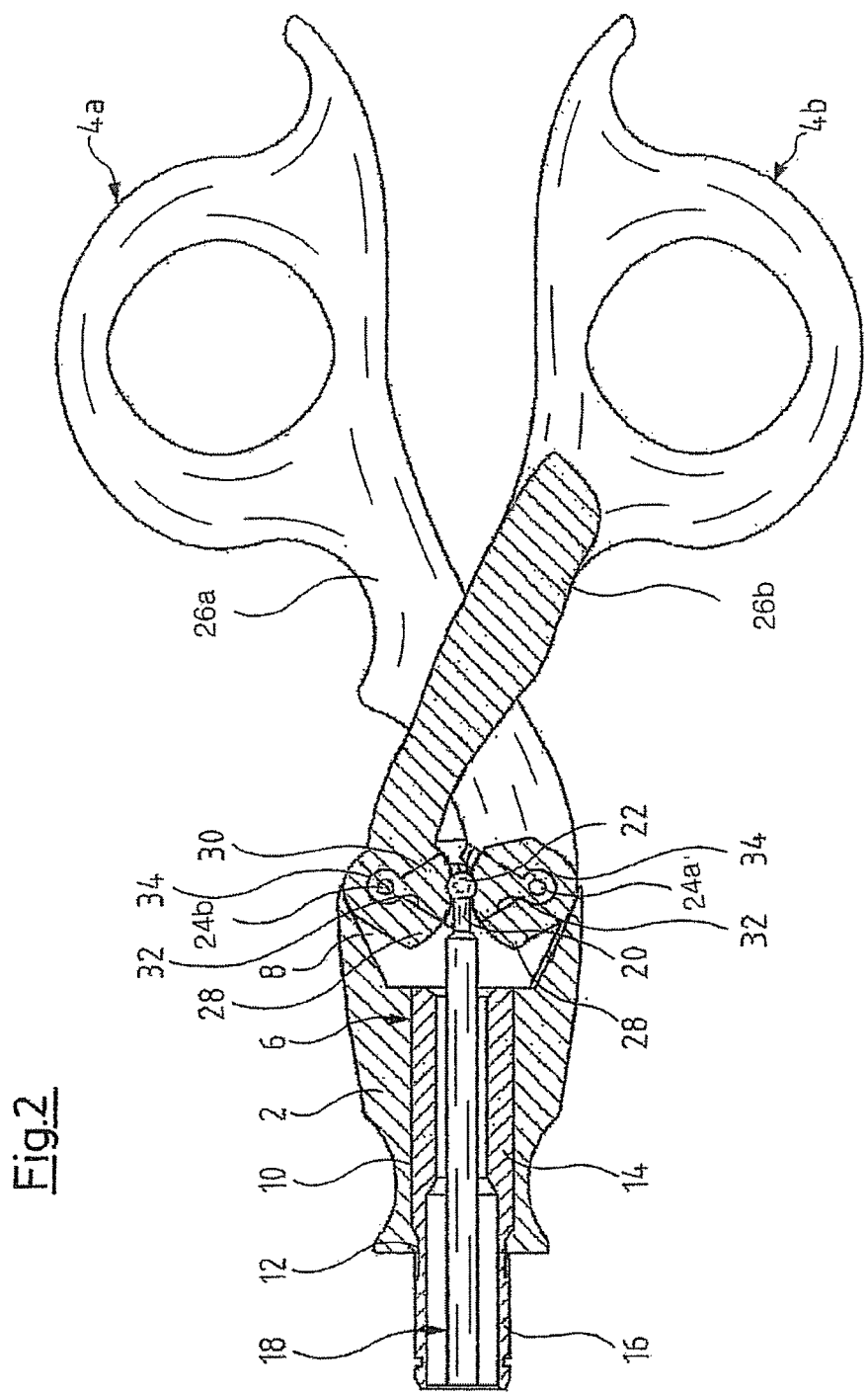
FIG. 2 is a partly sectioned side view of the operating part according to FIG. 1.
Figure 3:
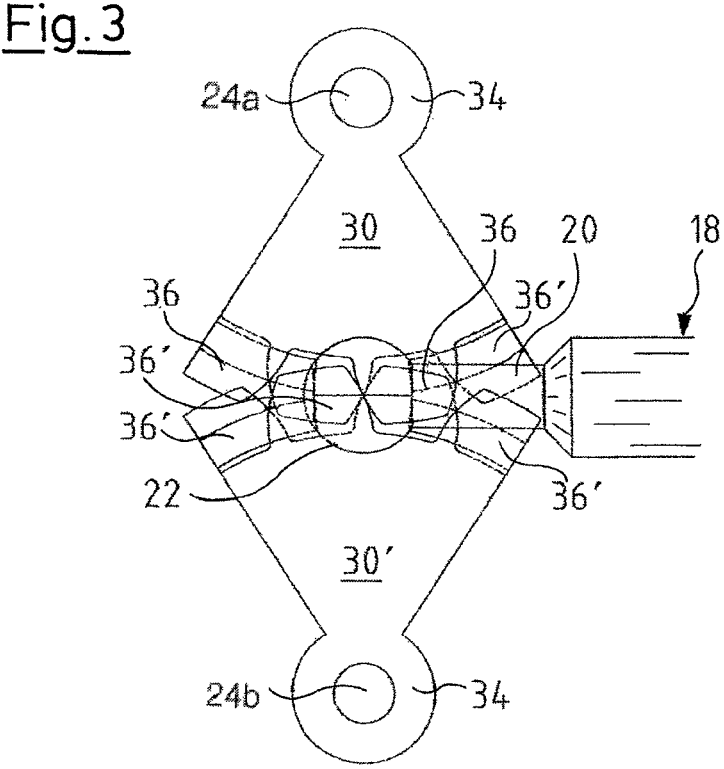
FIG. 3 is a basic representation of engagement conditions of two cog segments and an actuation element in the operating part according to FIG. 1, in a first engagement position.
Figure 4:
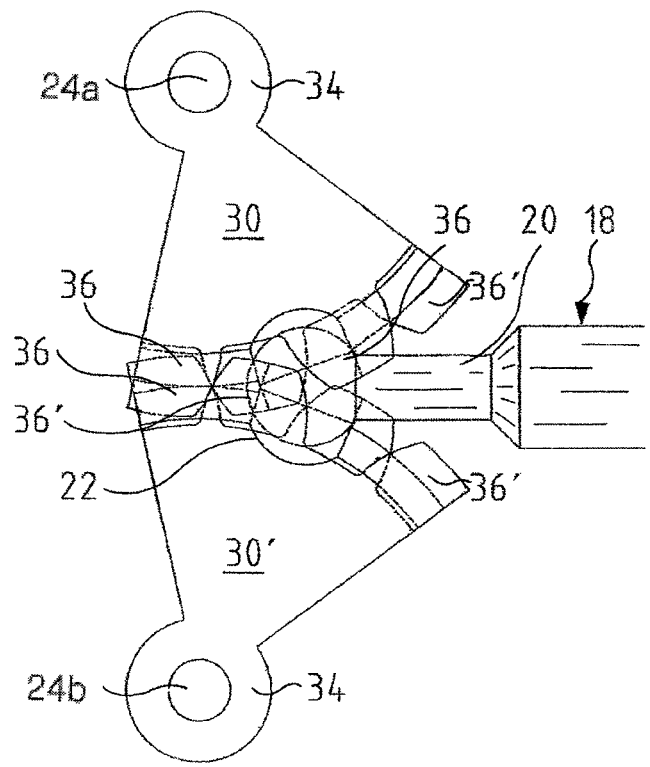
FIG. 4 is a basic representation of the engagement conditions of the two cog segments and the actuation element in the operating part of according to FIG. 1, in a second engagement position.

Referring to the drawings in detail, wherein like numerals indicate like elements throughout the several views, FIGS. 1 and 2 show an operating part of a medical instrument, according to a preferred embodiment of the present invention, which forms the proximal end of the instrument. With regard to the medical instrument, it is preferably an endoscopic shank instrument. An operating part preferably includes a connection part 2, on which two grip parts 4a and 4b are articulated.

As is to be deduced from FIG. 2, an opening 6 which extends in the longitudinal direction of the connection part 2 through this in a complete manner is formed on the connection part 2. On the proximal side, the opening 6 has a section 8 which departing from the proximal end of the connection part 2 continuously tapers in the distal direction. A cylindrical section 10 of the opening 6 connects to the section 8 on the distal side amid the formation of a shoulder. The opening 6 tapers conically distally of the section 10 and merges into a section 12.

A sleeve 14 is arranged in the opening 6 of the connection part 2, in the sections 10 and 12, wherein a distal end section 16 of the sleeve 14 projects out of the connection part 2 at the distal side. The end-section 16 serves for fastening a shank tube of the endoscopic shank instrument which is not shown in the drawing.

An actuation element 18 in the form of a pull-push rod is guided through this shank tube as well as through the inner lumen of the sleeve 14. The actuation element 18 is axially displaceable in the shank tube as well as in the connection part 2. The actuation element 18 extends through the complete shank tube, which is not shown in the drawing, and in the region of the distal end of the instrument is coupled in movement to a tool which is movably arranged there.

At its proximal end, the actuation element 18 has a section 20 with a cross section which is tapered with respect to the remaining actuation element 18. The proximal end of the actuation element 18 forms a spherical widening 22 which connects onto the section 20 of the actuation element 18. Two joint pins 24a, 24b are arranged distanced to one another in the section 8 of the connection part 2, in the direct vicinity to the proximal end of the connection part 2. The grip parts 4a and 4b are articulated on the connection part 2 in a pivotably movable manner, at these two joint pins 24a, 24b.

The grip parts 4a and 4b are in each case designed as a two-part lever. They each preferably each include a respective proximal lever arm 26a, 26b which is to be gripped manually, and a distal lever arm 28. The distal lever arms 28 of the grip parts 4a and 4b are each aligned essentially in the direction of the respective joint pins 24a, 24b, on which the respective other grip part 4a and 4b is articulated. Inasmuch as this is concerned, the distal lever arms 28 of the two grip parts 4a and 4b are aligned to one another between the joint pins 24a, 24b.

The distal lever arms 28 of the two grip parts 4a and 4b are directly coupled in movement to one another. For this purpose, the distal lever arms 28 in each case include teeth on the sides which face one another, wherein the two sets of teeth are engaged to one another. The teeth are formed by cog segments 30 and 30' which are integrated in recesses 32 of the distal lever arms 28. For reasons of a better overview, the teeth have not been shown in FIG. 2. This is, however, clear from FIGS. 3-9.

The cog segments 30, 30' have essentially the shape of a sector of a circle with an arc-shaped outer side, on which the teeth are formed and two straight outer sides which departing from the arc-shaped outer side taper to one another in a pointed manner and at whose ends a bearing lug 34 serving for receiving a joint pin 24a, 24b is formed. The outer sides of the cog segments 30, 30' which taper to one another in a pointed manner enclose an angle of 65°. The teeth of the cog segments 30, 30' are asymmetrical and are formed by two teeth 36, 36', respectively, and two tooth gaps 38, 38' respectively.

Figure 6:
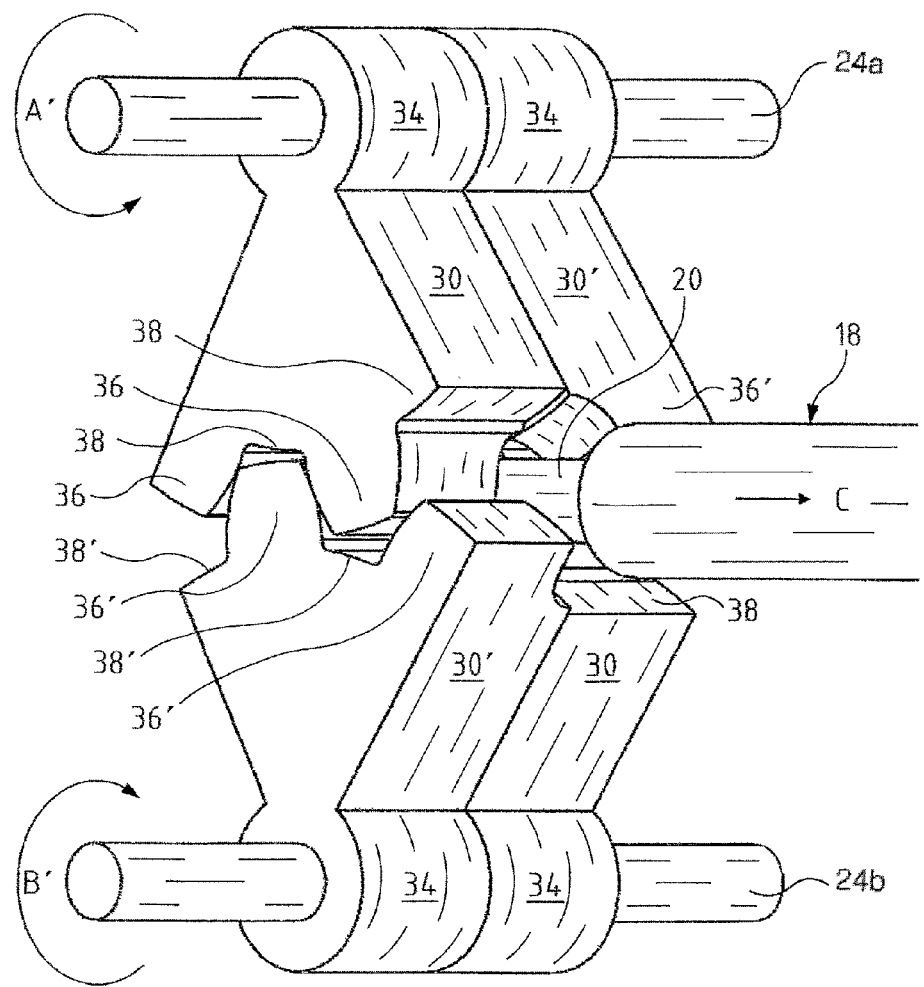
FIG. 6 is a perspective representation of the engagement conditions according to FIG. 3.
Figure 7:
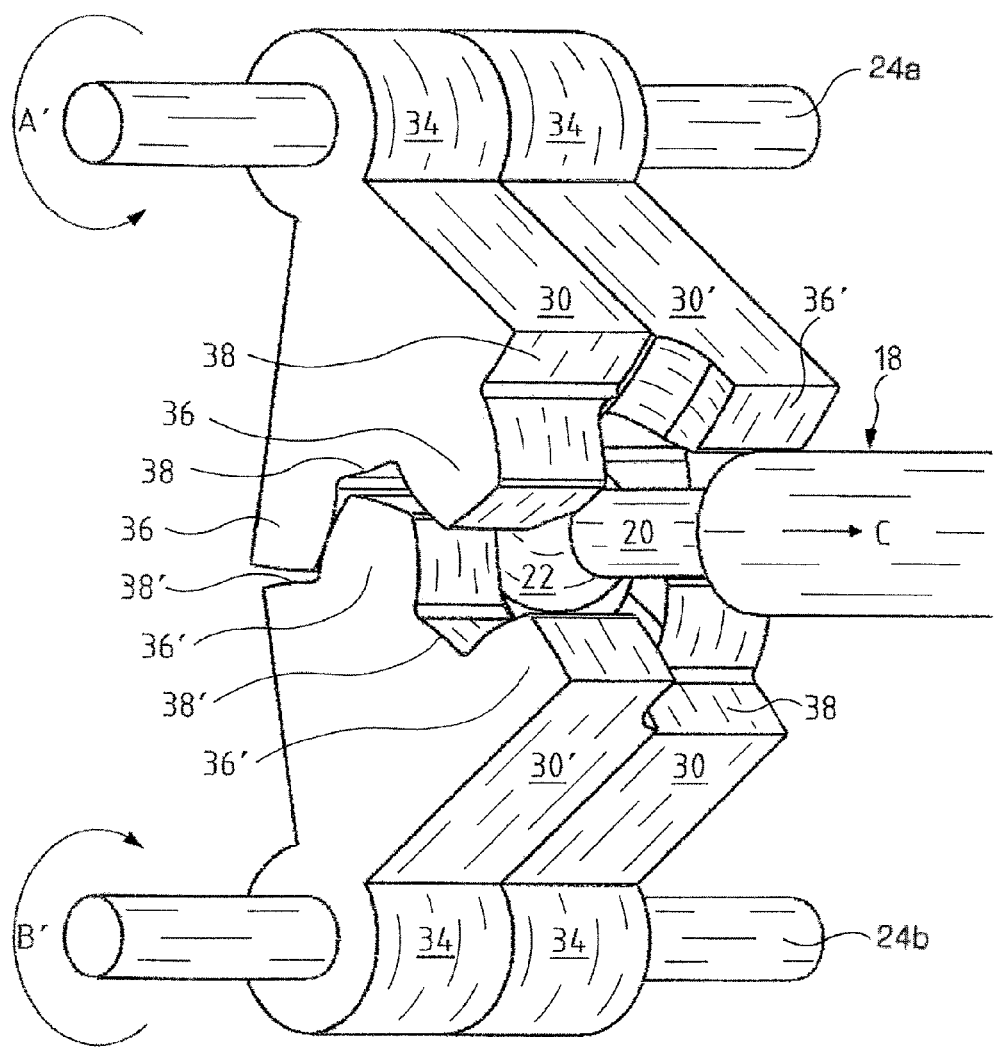
FIG. 7 is a perspective representation of the engagement conditions according to FIG. 4.
Figure 8:
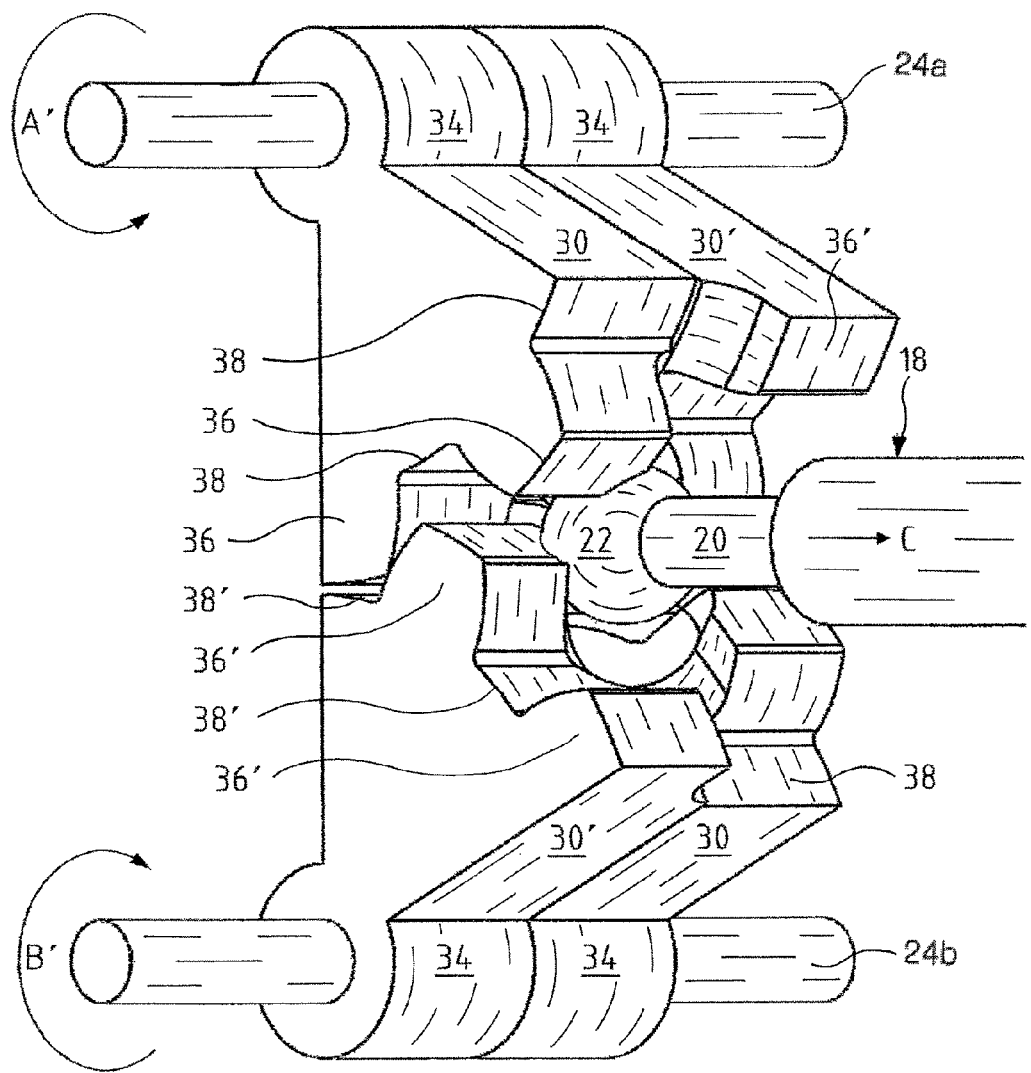
FIG. 8 is a perspective representation of the engagement conditions according to FIG. 5.

In each case, two cog segments 30, 30' are arranged over one another in the recesses 32 of the two distal lever arms 28, wherein a first cog segment 30 is arranged rotated by 180° to a second cog segment 30', so that a tooth 36' of the second cog segment 30' is arranged where a tooth gap 38 of the first cog segment 30 is located, and a tooth gap 38' of the second cog segment 30' is arranged located where a tooth 36 of the first cog segment 30 is located, which is particularly clear from the FIGS. 6-8. The cog segments 30 and 30' which are arranged in the distal lever arms 28 in each case are all designed in a constructionally equal, thus identical manner.

The distal lever arms 28 are also directly coupled in movement to the actuation element 18 via their cog segments 30 and 30'. Hereby, the actuation element 18 is guided between the cog segments 30 and 30' which are arranged lying opposite one another and are engaged with one another. For this purpose, recesses 40 which extend essentially over the complete tooth height of the teeth 36 and 36' (FIG. 9) are formed on the cog segments 30 and 30' on their teeth 36 and 36' in a manner departing from a flat side of the cog segments 30 and 30'. With two cog segment pairs of the distal lever arms 28 engaging into one another, the recesses 40 formed on the cog segments 30 and 30' together with the tooth gaps of these cog segments 30 and 30' form a guide channel for the section 20 of the actuation element 18.

A further recess 42 whose inner contour corresponds to the outer contour of the spherical widening 22 of the actuation element 18 is formed on each of the cog segments 30 and 30', for receiving the spherical widening 22 formed on the proximal end of the actuation element 18. Together, the recesses 42 of the cog segments 30 and 30' of the cog segment pairs of the distal levers 28, said segments being arranged over one another, form an essentially spherical receiver space, in which the spherical widening 22 of the actuation element 18 is arranged with a positive fit.

The manner of functioning of the medical instrument according to a preferred embodiment of the present invention is evident in particular from FIGS. 6 and 8. Starting from an initial situation shown in FIG. 6, the distal lever arms 28 with the cog segments 30 and 30' integrated therein in each case, by way of a pivoting of the grip parts 4a and 4b to one another, are pivoted such that the cog segment pair represented on the left in FIGS. 6 to 8 in the direction A, and the cog segment pair represented on the right in FIGS. 6 and 8 are moved in the direction B. By way of this, the receiver space, in which the spherical widening of 22 of the actuation element 18 is arranged with a positive fit and which is formed between the four cog segments 30 and 30' by the recesses 42 of these cog segments 30 and 30', moves by a certain amount linearly in the direction C, by which means the actuation element 18 is displaced in the distal direction (FIG. 7). Subsequently, the grip parts 4a and 4b can pivoted away from one another, by which means the actuation element 18 is displaced back in the reverse manner in the proximal direction again. If the lever arms starting from the condition represented in FIG. 7 are pivoted further forwards such that the tooth segment pair represented in FIGS. 6 to 8 on the left moves in the direction A and the tooth segment pair represented in FIGS. 6 to 8 on the right moves in the direction B, the inner walls of the recesses 42 formed on the cog segments 30 and 30' move away from the spherical widening 22 of the actuation element 42 in a manner such that the actuation element 18 is released from the cog segments 30 and 30' and can be removed from the medical instrument.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A medical instrument in the form of an endoscopic shank instrument comprising:
   an actuation element (18) axially displaceable in a shank;
   two lever arms (28) pivotably articulated in a manner distanced to one another, the lever arms positioned at the proximal side of the shank and forming part of a grip part (4a, 4b), the lever arms (28) being coupled in movement to the actuation element (18) and directly coupled in movement to one another;
   rolling surfaces rolling on one another and being formed on sides of the lever arms (28) which face one another, each rolling surface having a groove arranged on an outer side thereof; and
   a spherical widening (22) formed on the actuation element (18), and engaging into the grooves formed on the rolling surfaces.

2. The medical instrument according to claim 1, wherein the rolling surfaces are designed in a toothed manner.

3. The medical instrument according to claim 1, wherein the actuation element (18) is led between the rolling surfaces.

4. A medical instrument in the form of an endoscopic shank instrument comprising:
   an actuation element (18) axially displaceable in a shank;
   two lever arms (28) pivotably articulated in a manner distanced to one another, the lever arms positioned at the proximal side of the shank and forming part of a grip part (4a, 4b), the lever arms (28) being coupled in movement to the actuation element (18) and directly coupled in movement to one another; and
   rolling surfaces rolling on one another and being formed on sides of the lever arms (28) which face one another, wherein each rolling surface is formed of two parts arranged adjacent to each other in a direction of a pivot axis of each lever arm (28), wherein teeth are formed on a first part offset by a tooth gap width or tooth thickness with respect to teeth formed on a second part.

5. The medical instrument according to claim 4, wherein in each case two cog segments (30, 30') form the rolling surfaces of the lever arms (28), and wherein all cog segments (30, 30) are designed in a constructionally equal manner.

6. The medical instrument according to claim 5, wherein the cog segments (30, 30') have asymmetrical teeth.

7. The medical instrument according to claim 5, wherein each cog segment (30, 30') comprises two teeth (36, 36') and two tooth gaps (38, 38').

8. The medical instrument according to claim 5, wherein the cog segments (30, 30') enclose an angle of 65°.

9. The medical instrument according to claim 5, wherein the cog segments (30, 30') are integrated in the grip parts (4a, 4b).

\* \* \* \* \*